United States Patent
Baleine et al.

(10) Patent No.: US 8,866,084 B2
(45) Date of Patent: Oct. 21, 2014

(54) INFRARED NON-DESTRUCTIVE EVALUATION METHOD AND APPARATUS

(75) Inventors: Erwan Baleine, Orlando, FL (US); James F. Landy, Cape Canaveral, FL (US); Ching-Pang Lee, Cincinnati, OH (US); Stephanie Stinelli, Edgewater, FL (US)

(73) Assignee: Siemens Energy, Inc., Orlando, FL (US)

( * ) Notice: Subject to any disclaimer, the term of this patent is extended or adjusted under 35 U.S.C. 154(b) by 127 days.

(21) Appl. No.: 13/604,668

(22) Filed: Sep. 6, 2012

(65) Prior Publication Data

US 2014/0061476 A1   Mar. 6, 2014

(51) Int. Cl.
*G01J 5/02*   (2006.01)

(52) U.S. Cl.
USPC .......................................................... 250/340

(58) Field of Classification Search
CPC ....................................................... G01N 25/72
USPC .......................................................... 250/340
See application file for complete search history.

(56) References Cited

U.S. PATENT DOCUMENTS

| | | | |
|---|---|---|---|
| 3,283,148 A | | 11/1966 | Schwartz et al. |
| 3,566,669 A | * | 3/1971 | Sarcia et al. ...................... 374/5 |
| 3,798,366 A | | 3/1974 | Hunt et al. |
| 3,935,382 A | | 1/1976 | Hunt |
| 6,394,646 B1 | | 5/2002 | Ringermacher et al. |
| 7,040,808 B2 | | 5/2006 | Rehwinkel et al. |
| 7,064,331 B2 | | 6/2006 | Rothenfusser et al. |
| 7,069,169 B2 | | 6/2006 | Nakakita et al. |
| 7,312,454 B2 | | 12/2007 | Safai et al. |
| 7,671,338 B2 | | 3/2010 | Key |
| 7,771,777 B2 | | 8/2010 | Harris et al. |
| 8,244,488 B2 | * | 8/2012 | Allen et al. ...................... 702/47 |
| 2004/0056200 A1 | | 3/2004 | Rothenfusser et al. |
| 2009/0201971 A1 | | 8/2009 | Goldammer et al. |

FOREIGN PATENT DOCUMENTS

EP   1577505 A2   9/2005
EP   2031303 A1   2/2009

* cited by examiner

*Primary Examiner* — Constantine Hannaher
*Assistant Examiner* — Hugh H Maupin

(57) ABSTRACT

A method of nondestructive evaluation and related system. The method includes arranging a test piece (14) having an internal passage (18) and an external surface (15) and a thermal calibrator (12) within a field of view (42) of an infrared sensor (44); generating a flow (16) of fluid characterized by a fluid temperature; exposing the test piece internal passage (18) and the thermal calibrator (12) to fluid from the flow (16); capturing infrared emission information of the test piece external surface (15) and of the thermal calibrator (12) simultaneously using the infrared sensor (44), wherein the test piece infrared emission information includes emission intensity information, and wherein the thermal calibrator infrared emission information includes a reference emission intensity associated with the fluid temperature; and normalizing the test piece emission intensity information against the reference emission intensity.

20 Claims, 2 Drawing Sheets

INFRARED NON-DESTRUCTIVE EVALUATION METHOD AND APPARATUS

STATEMENT REGARDING FEDERALLY SPONSORED DEVELOPMENT

Development for this invention was supported in part by Contract No. DE-FC26-05NT42644, awarded by the United States Department of Energy. Accordingly, the United States Government may have certain rights in this invention.

FIELD OF THE INVENTION

The invention relates to nondestructive evaluation of test pieces. In particular, the invention relates to thermal calibration of infrared emission information from a test piece heated by a hot fluid flow.

BACKGROUND OF THE INVENTION

Hot air infrared thermography is one form of nondestructive evaluation of parts. In this method, hot air may be directed through an internal passage in a test piece in one or more pulses. During or after this pulse, an infrared sensor captures infrared emission information from an outside surface of the test piece. The infrared sensor is able to detect small variations in the infrared emission information indicative of different temperatures on the outside surface of the test piece. The infrared emission information can be used to generate a thermal image of the test piece in which the thermal variations across the surface of the test piece are visible. Areas of the outside surface nearer the internal passage will generally be hotter and therefore be visible in the thermographic image via a greater intensity. As a result the thermographic images can be used to evaluate internal passages of the test piece to determine, for example, its cooling efficiency, without any need to destroy the test piece.

Variations in testing conditions can lead to differences between thermographic images of the same test piece. For example, often a single test piece is subjected to several pulses of hot air in order to gain sufficient data for an accurate reading. The temperature of the hot air for each pulse may change due to the length of hoses, outside temperature, and compressor etc. Further, with each pulse the test piece heats up, and with each delay between pulses the test piece cools down, and thus the emission intensity of the test piece may change with each pulse. While a relative temperature distribution of the test piece will show in each of the thermographic images, an intensity level of the image may vary from image to image. This variation in intensity may be particularly prevalent near a cooling passage, which will heat up more quickly than the surrounding material. As a result, the cooling passages may vary in intensity from one image to the next relative to the surrounding material. This variation in intensity makes it difficult to detect certain partially blocked passages and measure wall thicknesses etc. Further, less accurate image data makes it difficult to compare thermal efficiency of different blade designs.

In addition, with no reference to the input air temperature, comparing multiple test pieces to each other on the same temperature scale difficult. Consequently, there is room for improvement in the art.

BRIEF DESCRIPTION OF THE DRAWINGS

The invention is explained in the following description in view of the drawings that show.

DETAILED DESCRIPTION OF THE INVENTION

Figure 1:
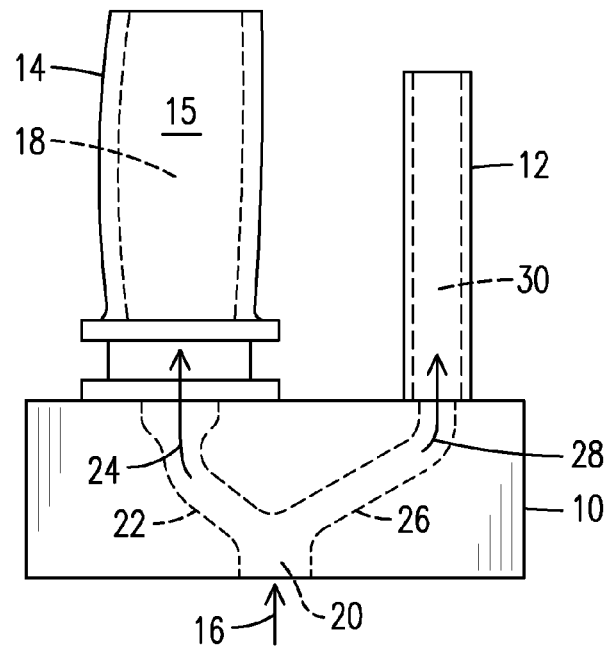
FIG. 1 shows an exemplary embodiment of a fixture of the non destructive testing apparatus.

The present inventors have devised a method and apparatus for calibrating infrared emission information of test pieces that overcomes the problems associated with varying test conditions. The method provides a thermal calibrator which generates infrared information fully correlated to a temperature range of the flow of hot air, and for each thermographic data capture, an intensity of infrared emissions of the test piece is normalized against an intensity of the infrared emissions from the thermal calibrator. For each capture of infrared emission information, the thermal calibrator is exposed to fluid originating from the same flow of hot air as the fluid used in the test piece, so the thermal calibrator's infrared emission intensity for a given capture is associated with a temperature of the flow of hot air used during the given capture. Consequently, when infrared emission intensity from the test piece is normalized against infrared emission intensity from the thermal calibrator during a capture, then the infrared emission intensity from the test piece is, in turn, normalized against the temperature of the flow of hot air for the capture. This provides not only an accurate representation of the relative temperature distribution throughout the test piece, but it allows for an intensity for any capture that is normalized to the thermal calibrator, and thus to the temperature of the flow of hot air during the capture. As a result, the normalized infrared image intensity for all captures does not vary in intensity with variations in the temperature of the input air. Consequently, a thermographic image generated from a single capture or from a plurality of captures will likewise not vary in intensity with variations in the temperature of the input air. In particular, an intensity of the cooling passages, which is most susceptible to variability in the input air temperature, will be normalized against the temperature of the input air. A repeatability study of the improved method described herein has demonstrated that the normalization process reduces variability from one capture to the next from above 20% to below 5%, and consequently this process represents a dramatic improvement in the art. It is important to note that an exemplary embodiment described herein may generate a thermographic image, however, the infrared emission information need not be converted into an image, but may instead be manipulated as disclosed in pre-image data form and then evaluated while still in data form.

Further, when the same thermal calibrator is used for differing test pieces, the capture information, and any thermographic images generated therefrom, of differing test pieces can be compared on a same scale since the temperature of the flow of hot air for each respective capture can be determined from the known infrared emission information of the thermal calibrator. This allows for more accurate comparison of one test piece to another as though they were tested under identical test conditions. The requirement that the same thermal calibrator be used is based on the thermal response characteristics of the thermal calibrator itself. More particularly, differing thermal calibrators may respond differently to a pulse of heated air and this would result in different reference intensity for identical pulses. For example, a relatively thin thermal calibrator may heat up more quickly than a thicker one, and thus a relatively thin thermal calibrator may result in a less intense test piece thermographic image than if the thicker thermal calibrator were used. In instances where the same thermal calibrator is used to test a first and a second test piece, the infrared emission information, and any thermographic images generated therefrom, can be compared simply by adjusting the first and second reference intensities to a common value on a scale. This will yield test piece intensity information about both test pieces on the same scale.

Both the prior art hot air thermography procedure and the method disclosed herein produce information regarding relative temperature distributions within a test piece. This is useful to determine if the test piece had, for example, a blockage in a single passage. In such a case the remainder of that passage would be represented as cooler on the thermographic image, and the operator would be alerted to the defect. However, under the prior art hot air thermography procedure it might not be possible to tell if, for example, a primary cooling channel that supplied all other channels was partially blocked. Specifically, if a first test piece had no blockages in a primary supply channel, a first thermographic image developed using a first flow of hot air at a given temperature would show internal channels at a first intensity on the thermographic image. However, if a second test piece had a minor blockage in the primary supply channel, a second thermographic image might show the internal channels at the same intensity as in the first thermographic image if the second flow of hot air were slightly hotter than the first flow of hot air. The increased temperature of the second flow of hot air would, in effect, compensate for the decreased flow volume through the main supply channel, and thus the first thermographic image and the second thermographic image may appear the same despite the fact that the second test piece has a partial blockage of the main supply channel.

Under the innovative method proposed herein, however, this partial blockage can now be detected using an absolute determination of temperature as described above. When using the thermal calibrator, the intensity of the cooling passages would be normalized against the temperature of the flow of hot air, and the first and second images could be compared by, for example, a second normalization where the reference intensity of each image is adjusted to a common value in one or more images. In this manner, or a similar manner known to those in the art, the cooling channels of the second test piece would be displayed with a lower intensity. As a result it would be evident that the second test piece had a reduced cooling efficiency when compared to the first, which would indicate a blockage in the primary supply channel.

FIG. 1 shows an exemplary embodiment of a fixture 10 of the non destructive testing apparatus. The fixture 10 is shown holding a thermal calibrator 12 and a test piece 14 having a surface 15. In this exemplary embodiment the test piece 14 is a blade. The fixture 10 is configured to position the test piece 14 and the thermal calibrator 12 in the field of view of an infrared sensor (not shown). The fixture is also configured to enable fluid communication between the supply 16 of heated fluid and an internal passage 18 of the test piece 14, (which is represented schematically), and enable fluid communication between the supply 16 of heated fluid and the thermal calibrator 12. In the exemplary embodiment shown in FIG. 1, fluid communication is established by a plenum 20 that receives the supply 16 of heated fluid and divides it into a first flow passage 22 that directs a first flow 24 to the internal passage 18, and a second flow passage 26 that directs a second flow 28 to an internal passage 30 of the thermal calibrator 12. In this manner, fluid from the supply 16 of heated fluid is directed to both the thermal calibrator 12 and the test piece 14. It is the fact that the fixture 10 is configured such that the thermal calibrator 12 and the test piece 14 are exposed to air emanating from the supply 16 of heated air that permits the relationship between the infrared emission intensity of the thermal calibrator 12 to be indicative of the temperature of the flow of air to which the test piece 14 is exposed. Consequently, any variations in a temperature of the supply 16 of heated fluid will be reflected in the thermal calibrator 12.

Figure 2:
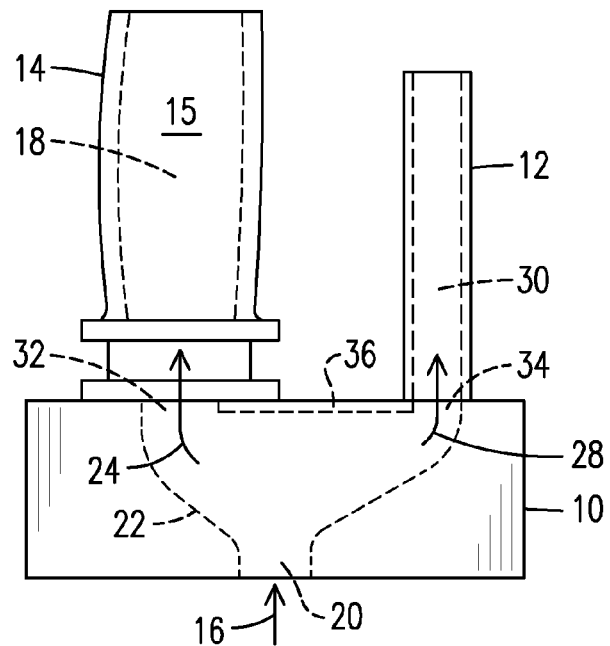
FIG. 2 shows an alternate exemplary embodiment of the fixture of the non destructive testing apparatus.

FIG. 2 shows a variation of the exemplary embodiment of a fixture 10 of FIG. 1. In this exemplary embodiment the plenum 20 receives the supply 16 of heated fluid and directs the first flow 24 directly from the plenum 20, through a first opening 32 to the test piece 14, and directs the second flow 28 directly through a second opening 34 to the thermal calibrator 12. The material in a region 36 between the first opening 32 and second opening 34 is at least sufficient to maintain structural integrity of the fixture 10, but need not be more substantial. Such a configuration dispenses with the separate first flow passage 22 and second flow passage 26, and this allows for the first flow 24 and the second flow 28 to be of an identical or nearly identical temperature.

Figures 3, 4, 5:
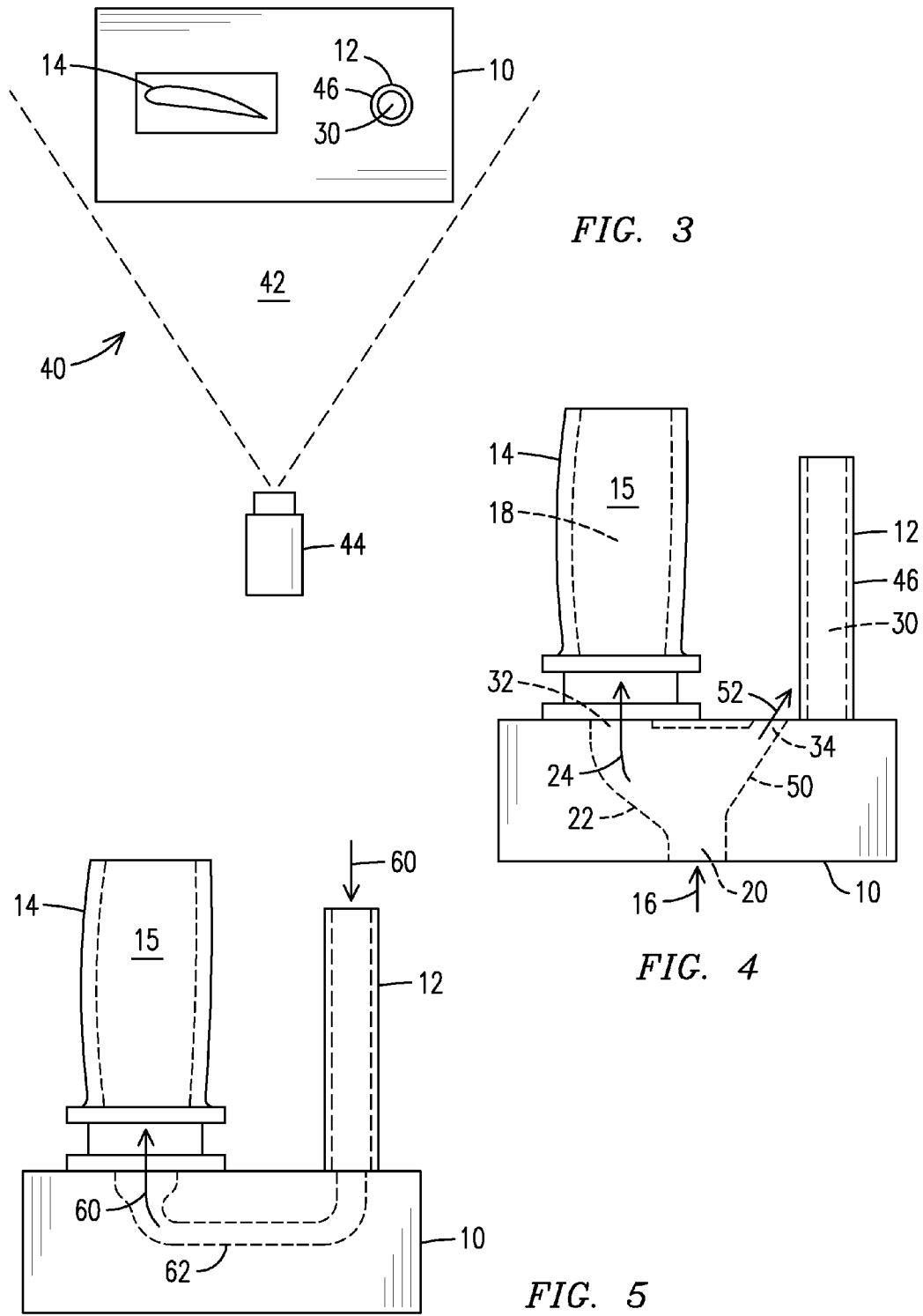
FIG. 3 shows an exemplary embodiment of the non destructive testing apparatus including a fixture positioned in a field of view of an infrared sensor.
FIG. 4 shows an alternate exemplary embodiment of the non destructive testing apparatus.
FIG. 5. shows another alternate exemplary embodiment of the non destructive testing apparatus.

FIG. 3 shows the non destructive testing apparatus 40 including the fixture 10, which holds the thermal calibrator 12 (having the internal passage 30) and the test piece 14 in a field of view 42 of an infrared sensor 44 such as in an infrared camera. In this manner infrared emission information radiating from both the thermal calibrator 12 and the test piece 14 can be captured on the same image. This eliminates any variability in responsivity of the infrared sensor 44 etc.

Infrared emission information from the thermal calibrator 12 will include infrared emission intensity information. A reference intensity can be selected from the thermal calibrator's emission intensity information. The reference intensity can be taken from a given location on the surface 46, and the given location may be a location having the highest intensity.

Infrared emission information from the test piece 14 will include infrared emission intensity information. To normalize the test piece infrared intensity information it may be divided by the selected reference intensity. For example, if infrared emission intensity information includes a plurality of data points of varying intensity, such as what might be represented as a pixel in a thermographic image, then an intensity of each data point/pixel may be divided by the reference intensity to reach a normalized infrared emission intensity for the test piece 14. The test piece infrared emission intensity information may also be normalized using other formulas known to those of ordinary skill in the art. A thermographic image may be generated from the normalized infrared emission information so that a human may evaluate the results, or the normalized infrared emission information may simply be manipulated in data form so that it may be automatically evaluated. Prior to the normalization step the infrared emission information may first be corrected for any background signal.

The thermal calibrator 12 may also be painted with a high emissivity paint. The paint ensures that the thermal calibrator 12 does not reflect outside infrared light. The thermal calibrator 12 may be configured such that any hot air exiting it does not heat the test piece 14. In an embodiment the thermal calibrator 12 may be a thin wall aluminum pipe (approximately 0.5 mm), and it may be sand blasted on the outside.

FIG. 4 shows an exemplary embodiment of a fixture 10 of the non destructive testing apparatus. Instead of having a second flow passage 26 that directs a second flow 28 to an internal passage 30 of the thermal calibrator 12, in this exemplary embodiment the second opening 34 directs a second flow 52 to impinge on a surface 46 of the thermal calibrator 12.

FIG. 5 shows another exemplary embodiment of a fixture 10 of the non destructive testing apparatus. Instead of dividing a supply of heated air into parallel flow passages, in this exemplary embodiment the thermal calibrator 12 and the test piece 14 are exposed to a single supply 60 of heated air in series. In the shown embodiment the single supply 60 of heated air first enters the thermal calibrator 12, travels through a connecting passage 62, and then the single supply 60 enters the interior of the test piece 14. Alternately, the single supply 60 could enter the test piece 14 first, then flow into the thermal calibrator 12 or impinge onto the surface 46 of the thermal calibrator 12. Any temperature loss in the single flow 60 resulting from heating the thermal calibrator 12 first, then the test piece 14, is considered negligible. Similarly, any difference in temperature drop along the first flow 24 and the second flow 28 is also considered negligible.

The thermal calibrator 12 operates as an air thermometer for the camera. However, it cannot be substituted by an actual thermometer, such as a thermocouple placed in the air flow. This is so because in the method disclosed herein the air temperature and the sample data are collected simultaneously using the camera infrared sensor. Any variation in responsivity is canceled out. This would not be the case using a thermocouple, for instance. Also, the thermal calibrator takes into account the averaging and Fourier transform processing of the hot air thermography data. Any thermocouple data would need to be time averaged with some unknown correction parameters. In addition, since the hot air is pulsed, the thermocouple would need a fast response time that is unlikely to be obtained. However, this is not a problem with the thermal calibrator. Further, any thermocouple device would need to be placed at a relevant location, but this has proven to be difficult due at least in part to flow disturbances. With the thermal calibrator the response is averaged over the entire flow. For these reasons as well as those detailed above this method and apparatus represent an improvement in the art.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method of nondestructive evaluation, comprising:
arranging a test piece comprising an internal passage and an external surface and a thermal calibrator within a field of view of an infrared sensor;
generating a flow of fluid characterized by a fluid temperature;
exposing the test piece internal passage and the thermal calibrator to fluid from the flow;
capturing infrared emission information of the test piece external surface and of the thermal calibrator simultaneously using the infrared sensor, wherein the test piece infrared emission information comprises emission intensity information, and wherein the thermal calibrator infrared emission information comprises a reference emission intensity associated with the fluid temperature; and
normalizing the test piece emission intensity information against the reference emission intensity to produce a normalized infrared intensity information for the test piece.

2. The method of claim 1, further comprising generating a thermographic image of the test piece using the normalized test piece emission intensity information.

3. The method of claim 1, further comprising dividing a flow of the fluid into a first flow and a second flow, exposing the test piece internal passage to the first flow, and exposing the thermal calibrator to the second flow.

4. The method of claim 1, further comprising sequentially exposing the test piece internal passage and the thermal calibrator to the flow of the fluid.

5. The method of claim 1, further comprising impinging a surface of the thermal calibrator with the fluid.

6. The method of claim 1, wherein the test piece emission intensity information comprises a plurality of pixels each comprising a pixel intensity, the method further comprising dividing each pixel intensity by the reference emission intensity to normalize the test piece infrared information.

7. The method of claim 1, further comprising capturing the reference emission intensity at a given location on the thermal calibrator.

8. The method of claim 1, further comprising capturing the reference emission intensity at a location of greatest infrared emission intensity.

9. A method of nondestructive evaluation, comprising:
arranging a first test piece and a thermal calibrator within a field of view of an infrared sensor;
generating a first flow of fluid characterized by a first fluid temperature;
exposing the first test piece and the thermal calibrator to fluid from the first flow;
capturing first infrared emission information of the first test piece and of the thermal calibrator simultaneously using the infrared sensor, wherein the first test piece first infrared emission information comprises first emission intensity information, and wherein the thermal calibrator first infrared emission information comprises a first reference emission intensity associated with the first fluid temperature;
normalizing the first emission intensity information against the first reference emission intensity to produce a first normalized infrared emission intensity information for the first test piece; and
generating a first thermographic image of the first test piece using the normalized first emission intensity information.

10. The method of claim 9, further comprising:
arranging a second test piece and the thermal calibrator within the field of view of the infrared sensor;
generating a second flow of fluid characterized by a second fluid temperature;
exposing the second test piece and the thermal calibrator to fluid from the second flow;
capturing second infrared emission information of the second test piece and of the thermal calibrator simultaneously using the infrared sensor, wherein the second test piece infrared emission information comprises second emission intensity information, and wherein the second infrared emission information generated by the thermal calibrator comprises a second reference emission intensity associated with the second fluid temperature;
normalizing the second emission intensity information against the second reference emission intensity; and generating a second thermographic image of the second test piece using the normalized second emission intensity information and using a same temperature scale as the first thermographic image.

11. The method of claim 10, further comprising ensuring that a first test piece flow path establishing fluid communication between the first flow of fluid and the first test piece is the same as a second test piece flow path establishing fluid communication between the second flow of fluid and the second test piece.

12. The method of claim 10, further comprising ensuring that a first thermal calibrator flow path establishing fluid communication between the first flow of fluid and the thermal calibrator is the same as a second thermal calibrator flow path establishing fluid communication between the second flow of fluid and the thermal calibrator.

13. The method of claim 10, further comprising comparing the first thermographic image to the second thermographic image.

14. A system for nondestructive evaluation, comprising:
an infrared imaging sensor configured to capture infrared information in a field of view;
a thermal calibrator configured to emit infrared information when exposed to a heated fluid; and
a fixture assembly configured to:
position a test piece and the thermal calibrator in the field of view, wherein the infrared imaging sensor is configured to simultaneously capture infrared emission information of the test piece external surface and the infrared emission information of the thermal calibrator;
receive a supply of heated fluid;
enable fluid communication between the supply of heated fluid and an internal passage of the test piece; and
enable fluid communication between the supply of heated fluid and the thermal calibrator,
wherein the infrared emission information simultaneously captured by the infrared imaging sensor comprises test piece pixel data indicative of emission intensity information of the test piece external surface, and further comprises reference pixel data indicative of reference emission intensity responsive to the fluid temperature, wherein the test piece pixel data and the reference pixel data are processed to produce a normalized infrared emission intensity information for the test piece.

15. The system of claim 14, wherein the system is further configured to receive a single flow of heated fluid in a plenum, and wherein the assembly further comprises a first hole configured to permit fluid communication between the plenum and the test piece internal passage, and a second hole configured to permit fluid communication between the plenum and the thermal calibrator.

16. The system of claim 15, wherein the second hole permits fluid communication between the plenum and an interior of the thermal calibrator.

17. The system of claim 15, Wherein the second hole is configured to direct at least a portion of the supply of heated fluid to impinge a surface of the thermal calibrator.

18. The system of claim 14, wherein the system is further configured to receive a single flow of heated fluid and divide it into a first flow path to the test piece internal passage and a second flow path to the thermal calibrator.

19. The system of claim 14, wherein the system receives a single flow and delivers at least a portion of the single flow to the test piece internal passage and to the thermal calibrator.

20. The system of claim 14, wherein the thermal calibrator comprises a surface painted with a high emissivity paint.

* * * * *